United States Patent [19]

Siddiqi

[11] 4,438,067

[45] Mar. 20, 1984

[54] TEST STRIPS FOR ANALYZING DISSOLVED SUBSTANCES

[75] Inventor: Iqbal Siddiqi, Veyrier, Switzerland

[73] Assignee: Battelle Memorial Institute, Switzerland

[21] Appl. No.: 372,796

[22] Filed: Apr. 28, 1982

Related U.S. Application Data

[63] Continuation of Ser. No. 193,271, filed as PCT EP/00035, May 16, 1979, published as WO 79/01081, Dec. 13, 1979, § 102(e) date Dec. 27, 1979.

[30] Foreign Application Priority Data

May 17, 1978 [CH] Switzerland ..................... 5334/78

[51] Int. Cl.³ ............... G01N 21/78; C12Q 1/54; C12Q 1/26; C12Q 1/28; C12Q 1/30; C12N 11/04; G01N 35/22
[52] U.S. Cl. ............................. 422/56; 422/57; 435/14; 435/25; 435/27; 435/28; 435/182; 435/805; 435/810; 436/66; 436/95; 436/169
[58] Field of Search ............ 435/4, 14, 25, 26, 27, 435/28, 182, 805, 810; 422/55, 56, 57, 61; 436/23, 63, 66, 829, 94, 95, 169

[56] References Cited

U.S. PATENT DOCUMENTS

| Re. 30,267 | 5/1980 | Brushi | 422/57 |
| 3,092,463 | 6/1973 | Adams et al. | 422/56 |
| 3,639,306 | 2/1972 | Sternberg et al. | 435/182 |
| 3,691,090 | 9/1972 | Katajima et al. | 435/182 |
| 3,926,732 | 12/1975 | Rosen et al. | 435/14 |
| 4,046,514 | 9/1977 | Johnston et al. | 435/14 |
| 4,258,001 | 3/1981 | Pierce | 435/805 |

OTHER PUBLICATIONS

Chang et al, "Semipermeable Aqueous Microcapsules", Can. J. of Physiol. Pharm., vol. 44 (1966), pp. 115–128.

Primary Examiner—Esther M. Kepplinger
Attorney, Agent, or Firm—Karl F. Ross; Herbert Dubno

[57] ABSTRACT

Test strip for the dip and read colorimetric determination of substances dissolved in liquids. Such strips are composed of an inert supporting base covered with a layer of polymer beads in which the reagents are incorporated. The color reaction takes place within the beads themselves which improves sensitivity and reproducibility of the testing.

7 Claims, 3 Drawing Figures

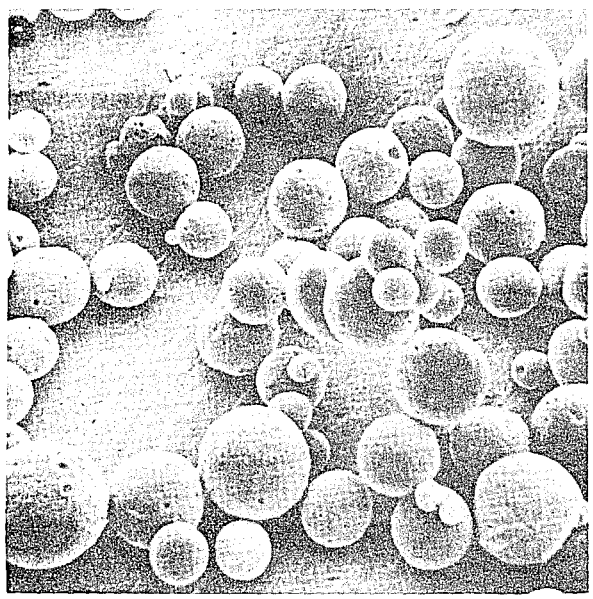
FIG. 1     200x
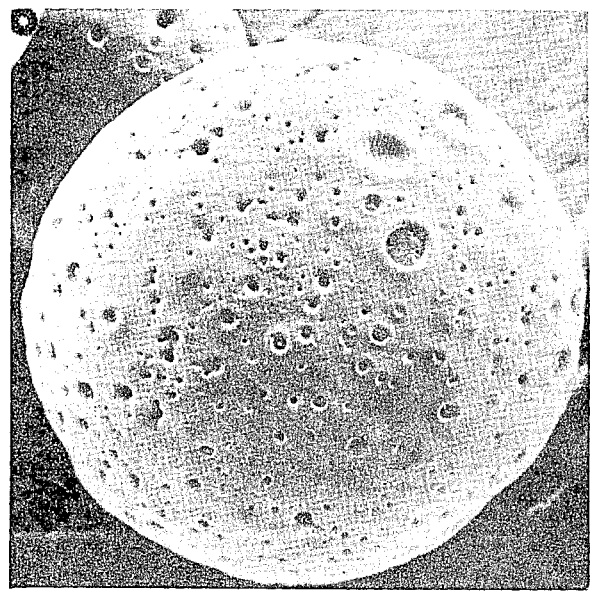
FIG. 2     950x

TEST STRIPS FOR ANALYZING DISSOLVED SUBSTANCES

CROSS REFERENCE TO RELATED APPLICATIONS

This application is a continuation of Ser. No. 193,271 filed Jan. 17, 1980 (now abandoned). This latter application was, in turn, an international phase application based upon PCT/EP79/00035, filed May 16, 1979 and based, in turn, on a Swiss national application Ser. No. 5334/78 filed May 17, 1978.

TECHNICAL FIELD

The present invention concerns test strips for evaluating substances dissolved in aqueous solutions, for instance biological fluids. Strips of this kind, are generally made from a thin porous rigid or flexible laminated material in which reagents are incorporated, said reagents being responsible for the development of typical color reaction when the strip is contacted with the substances to be analyzed, for instance by dipping the strip into an aqueous solution of said substances. Such strips are particularly useful for making rapid qualitative or semi-quantitative determinations in medical diagnosis. A typical example of determination is the checking of blood or glucose in urine.

There exists already many models of commercial strips for achieving the above purpose, among which the following can be mentioned.

BACKGROUND OF THE ART

U.S. Pat. No. 3,092,463 discloses the use of strips for analyzing some blood constituents. These strips are made of filter paper impregnated with different reagents such as encapsulated hydroperoxides, an indicator (o-tolidine) and a buffer (citrate). Under normal storage conditions, no reaction occurs between the reagents and no discoloration of the indicator is observed but when the strips are dipped into a solution containing a substance to be analyzed, e.g. the prosthetic groups of blood, the capsules break hydrolytically with consecutive liberation of the hydroperoxide and a color reaction with the indicator is allowed to develop. However, these strips have the disadvantages that the filter paper (bibulous material) which supports the reagents often contains impurities which may interfere with the color development and, further, its sampling capacity for the solution to be analyzed is not well constant from test to test because of unavoidable differences in the fibrous material used for making the strips; thus the method is only qualitative. Another disadvantage is that the encapsulation is performed by means of a colloid substance such as gelatin, gum arabic or carboxy-vinyl polymers that produces very fragile thin walled capsules of questionable mechanical and storage stability. Another disadvantage is that the color will develop within the bibulous material itself which is often opaque and not homogeneous, thus introducing further sources of errors in the color evaluation.

U.S. Pat. No. 3,926,732 discloses the use of test strips for the color determination of catalase in milk. This method is based on the catalase dependent inhibition of the color reaction involved upon oxidation of a leuko-dye (o-tolidene) by hydrogen peroxide in the presence of peroxidase. In one embodiment of said reference, the strips comprise an inert solid absorption and diffusion medium in which are embedded physically separated individual microcapsules. The microcapsules are of the "Semi-permeable aqueous" type (see Can. J. Physiol. Pharmacol. 44 (1966), 115) and the medium is made of cellulose fibers. When the strip is dipped into the solution to be analyzed, the hydrogen peroxide generated by the reagents of a first kind of microcapsules will migrate through the medium whereby it will be partially inhibited in proportion to the amount of catalase to be analyzed and, finally, it will react with the dye having diffused from microcapsules of a second kind. The color will then be released within the diffusion medium with consecutive disadvantages as mentioned heretofore. Also in this method the sampling capacity of the strip per unit area is very difficult to keep constant and the method is not accurate. Another disadvantage of the strips involving layers of fibrous absorbing media is the face that such media have a largely opened structure which does not adequately filter out unwanted colored species which may be present in the liquid to be analyzed and which may interfere with the desired color reaction. This has been partly remedied by using strips with a low porosity media layer in which the reagents are dispersed or dissolved. Such kinds of strips are disclosed for instance in U.S. Pat. No. 3,630,957, but they have the drawback that they possess no instant sampling capacity for the liquid to be analyzed. Indeed, when such strips are immersed in said liquid, the latter will slowly penetrate into the pores of the medium (in the range of 0.1–1 $\mu$m) and the substances to be analyzed will diffuse toward the reagents leaving out the possibly interfering materials. However, this process will take several minutes or more and it is not possible to exactly say at which time the process is really effective and when the color is sufficiently developed. Therefore, the test is slow and qualitative only. Some of the above drawbacks can be obviated by depositing a drop of the liquid to be analyzed on the strip. However, this is also a slow process and there is no way to tell that the drop will always be absorbed by a known given area of the strip; therefore the test is also qualitative only.

The above disadvantages have been partly cured by using the strips disclosed in French Pat. No. 2,303,290. These strips comprise as a diffusing medium a synthetic polymer obtained by the phase inversion precipitation technique. According to this technique, a solution of a polymer is prepared in a mixture of two solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous gelled bibulous structure resembling cellulose fibers and having favorable sampling properties for the liquid to be analyzed. The reagents necessary to develop the analytical color reactions of the strips can be either incorporated by impregnation or by dissolving into the original polymer solution. This is advantageous because, in case of mutually incompatible reagents, one of which can be put within the body of the polymer itself whereas the other can be imbibed in the opened porous structure whereby contact between said reagents in the dry state under storage is minimized. These strips have many advantages, however the intimate structure and the porosity of the matrix is strongly dependent on the preparative conditions and reproducibility of the specifications is difficult to maintain from batch to batch. Also, because of its rather fibrous nature, this material can introduce differential diffusion effects on the solution to be analyzed which can be a source of inconsistency in color development. Further, the color develops within the full body of the absorptive medium which, because of light diffraction problems related to the structure thereof, may limit the sensitivity in some cases.

U.S. Pat. No. 3,993,451 discloses test strips an embodiment of which comprises a strip of hydrophilic paper coated, on one side, with a uniform layer of a homogeneous mixture of two kind of particles. These particles are formed of agglomerates of hydrophilic absorbent materials such as powdered cellulose, alumina, silicagel, etc . . . impregnated by the reagents solutions and dried thereafter. One kind of the particles contain a first reagent and the second kind of particles contain a second reagent, said two reagents being not compatible and being thus kept apart during storage. When dipped into the solution to be analyzed, a portion of said solution is sampled by the absorbent materials and the reagents are allowed to contact the substance to be tested with consecutive development of the color reaction. This color test is therefore very fast but the sampling action is rather erratic because of the powdery nature of the absorbent material and the uncontrolled size of the agglomerates containing the reagents.

The present invention has for object to correct as much as possible the above discussed deficiencies. Briefly summarized an ideal test strip would fullfil the following needs and properties:

(a) Accurately sample a given amount of solution to be analyzed per unit area of the strip.

(b) Achieve such sampling instantaneously in the course of one single move: dip and withdraw.

(c) Allow intimate contact between the substance to be analyzed and the reagents and filter out undesirable component of the solution which may interfere with the desired analytical reactions.

(d) Allow rapid and reproducible color development with good sensitivity and good measurability (visual or spectrophotometer).

(e) Allow good separation under storage of reagents when mutually incompatibles.

(f) Accomodate reagents of different compatibilities, e.g. water-soluble reagents and liposoluble reagents.

(g) Avoid as much as possible so called "inert" media which may mask or interfere with the color reaction.

(h) Offer simple and economic fabrication routes.

(i) Be strong enough mechanically to withstand accidental abuse (rupture by abrasion).

(j) Have a long shelf-life, i.e. have reagents well shielded and preserved from evaporation or decomposition.

DISCLOSURE OF THE INVENTION

The test strip of the invention is a very valuable approach to the above requirements. This strip essentially encompasses a supporting non porous, non absorbant base substrate, e.g. a plastic sheet or strip coated (at least on one side) with a continuous layer of polymeric hydrophilic microspheres or beads, the reagents necessary for achieving the desired analytical color reactions being incorporated in said beads. Alternatively, the base material could be a metal sheet, e.g. an aluminum sheet or a glass sheet. The beads are simply attached by adhesion to the supporting strip without any dispersive and absorbent matrix for embedding the beads like in the strips of the prior-art in which said matrix serves usually as a sampling medium for the solutions to be tested and also as a development medium for the desired colored analytical reaction. Therefore, in the strip of the invention, the color will develop within the beads themselves which is much advantageous with respect to color development reproducibility because an erratic spreading of the reagents is thus strongly minimized. Further, despite the lack of an absorbent medium, the present strip displays a very accurate sampling capacity. In this connection, it should be noted that the absorbent power of the beads themselves (or rather of the hydrophilic polymer which constitutes the beads) has no particular influence, because it is the space between the beads which is adapted for achieving the sampling action on the solution to be analyzed. This is possible because the beads are made of a hydrophilic polymer which gets wetted by said solution when the strip is immersed therein and which will therefore instantaneously retain a constant portion of liquid per unit area due to capillary effects. Therefore, depending on the wetting properties of the polymer used and on the beads average diameter, the amount of liquid sampled per unit area of the strip can be determined and kept under control. For this, the beads will preferably have a uniform average diameter and they will be applied on the strip in a uniform fashion, e.g. as a monolayer coating. In such case, the space between the beads will result from placing the beads on the strip in substantially close relationship to each other so as to provide between the beads on said strip voids of regular distribution. The sum of these voids will furnish a constant volume per unit area to be filled by the solution to be analyzed when the strip is dipped therein. The beads will be adhered to the strip preferably by means of an adhesive but other means such as, for instance, heat softening the surface of the plastic supporrt to the point that the beads will directly adhere thereto is also possible. It should be remarked at this stage that the principle of putting beads side by side on a strip to achieve a sampling action on a liquid is not novel per se. It has been disclosed for instance in French Pat. No. 2,191,734 which teaches a strip for detecting and evaluating substances by applying a drop of a solution of said substances on the strip and spectrophotometrically determining the color developed by some reaction between reagents of the strip and said substances to be analyzed. In the strip of this patent, there is at least three layers having independent functions: one of the layers serves as a reagent holding medium, a second layer serves as a filter element and a third external layer function as a distributing medium for equally spreading the liquid to be analyzed on the surface of the strip. This effect is obtained by using spherical beads of glass or polymer resin placed side by side as a spreading layer and coated onto the surface by means of an adhesive. However, it is said nowhere in the reference that such beads can also contain the analytical reagents of the strip like in the invention.

Preferably, in the invention, the size of the beads and the chemical nature of the polymer are selected for having the sampled liquid penetrate the beads at a rate sufficient to have an observable color develop within a minute or so. The polymer therefore must be adequately structured (semi-permeability) and, in these conditions, the unwanted materials possibly present in the solution will be filtered out because the polymer is adapted for allowing the substances to be analyzed to diffuse into the beads and for blocking other substances of larger molecular weights (proteins or red cells which are constituents of blood for example). Some data relative to the positioning of the reagents within the beads will be provided hereinafter.

The beads can all be of the same kind and contain the reagents all mixed together if they are mutually compatible or separated from each other if necessary; the method for achieving this separation will be described hereinafter. Alternatively, the beads can be of different kinds, i.e. one kind will contain one of the reagents and another kind will contain another reagent, said reagents being possibly not compatible with each other. In such case, the color will develop in one kind of the beads only but this is of no importance because the beads can be made small enough ($\sim$20–200$\mu$) for having the colored area to appear uniform.

Normally, for good color observation, the polymer used for the beads is preferably transparent or translucent and, in such case, the plastic sheet supporting the beads can be made opaque for better reflectivity, e.g. with titanium dioxide or any other opaque filler ($BaCO_3$, $CaSO_4$, paper coating pigments etc . . . ). Surprisingly enough, it has been found that the $TiO_2$ can also be incorporated within the beads, if desired, which is possible because the site of the beads which is the most important for color development is near the periphery thereof i.e. the presence of the white pigment in the beads has no detrimental effect on the observation of the color but rather enhances the contrast.

The polymer of the beads of the present strips can be selected from most water-insoluble hydrophilic polymers provided they can be dissolved in non-miscible organic solvents for reasons which will be discussed hereinafter. As such, products derived from cellulose, hydroxyacrylic polymers, polyalkylene-oxy polymers and polyamides can be used. In the cellulose group, cellulose esters and ethers such as methylcellulose, ethylcellulose, butylcellulose, cellulose acetate, propionate and butyrate can be used. The amount of the reagents which can be incorporated in the beads is extremely variable and, of course, depends on the particular reagents solubility, the sensitivity to be given to the tests and other needs which will appear to people skilled in the Art from case to case. This will be illustrated in the Examples hereinafter.

BEST MODES OF CARRYING OUT THE INVENTION

The method for preparing the beads is derived from known procedures and, more particularly, from the following reference: T. M. S. CHANG: "Microencapsulation of Enzymes and Biologicals", from METHODS IN ENZYMOLOGY, vol. 44 (1976), p. 210. The method used depends on the particular product desired. Thus, in one particular embodiment of the invention, a test strip was designed for ascertaining glucose in urine. The chemical reactions involved were the classical oxidation of glucose in the presence of a glucose-oxidase and the detection of the hydrogen peroxide liberated by means of o-tolidine in the presence of peroxidase. For making the beads, an ester of cellulose was selected and dissolved in a water-immiscible organic solvent containing o-tolidine. Then, a buffered water phase containing the enzymes was emulsified within this organic solution, thus forming droplets of the water phase within the organic solution. Thereafter this emulsion was again dispersed in a second water phase which resulted in the formation of polymer solution drops in said second water phase, each of said drops still containing, suspended therein, the droplets of the first water phase. Then, the dispersion was subjected to evaporation whereby the organic solvent was removed, thus providing hard cellulose ester beads containing small vacuoles filled with the water solution of the enzymes. The o-tolidine stayed dissolved in the polymer resin itself and thus was kept apart from mixing with the enzymes. The beads were filtered, dried and subjected to calibration with proper wire-mesh sizes, the beads in the 100 $\mu$m region being selected. Then the beads were applied as a continuous monolayer coating on a plastic support strip using an adhesive. As such, any usual adhesive in liquid form can be used, e.g. solutions of carboxymethylcellulose (CMC), polyvinylalcohol (PVA), gum arabic, butadiene-styrene rubber (3M), etc . . . In order to bond the beads to the plastic strip, a very thin layer of the adhesive solution can be sprayed or otherwise deposited on the latter and the beads are regularly adhered thereto using moderate pressure and an equalizing flat surface. In this case the beads were applied as a monolayer, the beads substantially touching each other in a continuous fashion. Alternatively, the beads can be wetted with a diluted solution of the adhesive and applied on the plastic strip with a doctor-knife or any similar tool. In this case thicker layers of beads (double or triple layers) can be contemplated.

When under use, the strip is dipped into the solution containing the glucose and immediately withdrawn. Then it is allowed to stand for a given time sufficient to enable the solution trapped in the space between the beads to penetrate the beads themselves and reach the vacuoles containing the enzymes. There, the reactions occur and the oxygen liberated by the peroxidase acting on the $H_2O_2$ generated by the oxidation of glucose will convert the o-tolidine located in the near vicinity of the vacuoles to the desired blue dye. On a practical standpoint, in order to have the color develop with a reasonable time, say one minute, the depth at which the substance to be analyzed must penetrate into the polymer to substantially reach the reagents of the beads should be about a fraction of a micron to one micron. Therefore, the thickness of the semi-permeable membrane protecting the vacuoles situated within easy reach from the outside should preferably be comprised between 0,1 $\mu$m and 1 $\mu$m.

In another embodiment, a strip was fabricated involving the use of two mutually uncompatible liposoluble reagents. In this case a first kind of beads were prepared by dissolving a polymer and the first reagent in a suitable non water-soluble solvent. This solution was dispersed in a water phase and thereafter subjected to evaporation which produced an aqueous dispersion of polymer beads of essentially uniform size (about 60 $\mu$m) containing the first reagent in the dissolved state. These beads of the first kind were then filtered, dried and calibrated. Beads of a second kind were made identically but with incorporation of the second reagent. After drying, both kinds of beads were mixed in proportion such that suitable equivalent amounts of the reagents were present in the mixture, then the latter was used to prepare the test strips as described hereinabove in the case of the first embodiment. The field use for the strips of both these embodiments will be described hereinafter in more detail.

In the preparation of the beads discussed above, many solvents insoluble in water but having good dissolving power for the hydrophilic polymers selected can be used; as such chlorinated solvents such as methylene chloride, chloroform and trichloroethylene can be used, as well as esters and ethers such as ethyl acetate, butylacetate, diethylether, etc. In general such solvents must be volatile enough to be removed by evaporation under gentle heating and air blowing or reduced pressure.

For carrying out the emulsion and dispersion operations mentioned above the use of emulsifying agents is strongly recommended. As such most usual commercial emulsifying agents with neutral properties are convenient, e.g. sodium-lauryl sulfate, "Tween 20" (made by ICI), etc . . .

It can be seen from the above description that the objects of the present invention are substantially fulfilled by the present strip components. Thus, due to the presence of hydrophilic beads arranged regularly on a non porous water impervious supporting plastic film, an accurate and fast sampling of the liquid to be analyzed is achieved. Then, because of the polymer intimate structure resulting from the method of preparation, the reagent will be efficiently separated and shielded under storage (fundamentally important when storing together a hydroperoxide and an oxidizable indicator) although the beads will allow intimate contact of the substances to be analyzed with the reagents contained in the beads and simultaneously exclude unwanted materials. Further, the concentration of the reagents near the surface of the beads will be sufficient for obtaining useful color developments with a penetration of the solution to be analyzed involving only a small fraction of the total thickness of the beads. In this respect, it should be pointed out that also with regard to contact surface considerations, there is a significant difference between the prior-art and the invention. In the prior-art, the observable reagent containing surface is a flat surface the absorbent powder and the reflectivity of which is related to its planar dimensions; In the invention, the surface is not flat but constituted by a succession of spherical beads the total surface of which is equal to $4\pi r^2$ (r being the radius of the beads). It can be easily calculated that the ratio of the area of said beads to the area of the surface supporting said beads is $\pi$, i.e. the available area is now more than 3 times the area available in the strips of the prior-art. Also from the color observation stand point, it can be calculated that the observable area from an array of beads on a flat surface visible from the outside is about 1.4 times that of the flat surface itself; therefore the observable color density and sensitivity will be increased as compared with the strips of the prior-art.

It can also be pointed out that in most test-strip embodiments of the prior-art, the bibulous materials used for sampling the solution to be analyzed will have to simultaneously accommodate the compound to be detected, the dye and the other reagents. Further such materials have a great internal contact surface and generally lack homogeneity because they cannot well reconcile two opposing properties: a high absorption capacity for the liquid to be analyzed and an equalizing action on the migration rates of the various chemicals involved (no chromatography effects). All such drawback have been eliminated in the invention. Also, in the invention the reproducibility in color development will be good because of the relatively narrow space concentration of the colored sites and the avoiding of the diffusion of the color outside the beads. Another favorable feature is the complete suppression of the fibrous embedding matrix of the strips of the prior-art, thus avoiding the differential diffusion effects related to the chromatographic properties of such fibrous media.

Finally, the strips used in the invention can be fabricated very simply and economically since they involve only two constructive elements i.e. the beads and the supporting strips, said beads being of a strong and resistant structure as compared with the frangible microcapsules of the prior-art. In such beads, the reagents are well shielded from the outside and the present strips have a very long shelf-life without modification of their analytical properties.

The following Examples illustrate the invention.

INDUSTRIAL APPLICATIONS

Example 1

Two g of cellulose triacetate and 0,25 g of o-tolidine were dissolved in 50 ml of $CH_2Cl_2$ with 0,1 g of a surfactant ("Tween 20" from ICI=polyoxyethylene-sorbitan monolaurate) to form a polymer solution (solution A).

A water solution was prepared by mixing together 3.5 ml of glucose-oxidase solution at 1000 I.U./ml, 60 mg of peroxidase (60 I.U./mg) and 185 mg of a citrate buffer (pH 4.7). This gave solution B.

Solution B was then emulsified in solution A under the following conditions: temperature: room temperature, stirrer: 2000 rpm, time: 20 min. The emulsion consisted in droplets of the B solution (1–5 $\mu$m) suspended in the polymer organic solution. Then this emulsion was dispersed in a second aqueous phase consisting of 460 mg of sodium-lauryl sulfate in 800 ml of 0.1 M aqueous acetate buffer, care being taken not to stir too fast in order to avoid obtaining too small particles. This dispersion consisted thus in drops of the organic solution A suspended in the second phase, each drops containing, evenly distributed, the droplets of solution B.

The dispersion was heated under agitation to 35° C. for 30 min while air was blown at the surface. The $CH_2Cl_2$ was progressively driven off which resulted in the formation of solid polymer beads containing the o-tolidine and solution B of the enzymes as tiny vacuoles trapped within the microporous body of the beads. When the $CH_2Cl_2$ was completely removed (which can be ascertained by the smell of the solvent), the beads were filtered and dried. They were examined under the microscope and were shown to have diameters ranging from about 40 to 100$\mu$ with the vacuoles situated near the periphery quite visible, the membrane separating said external vacuoles from the outside being only a fraction of a $\mu$. Such configuration is illustrated by the photographs taken with a scanning electron microscope and given in annexe:

FIG. 1 represents the beads at 200× magnification and shows the size distribution thereof.

FIG. 2 is an enlargement of one of the beads of FIG. 1.

Figure 3:
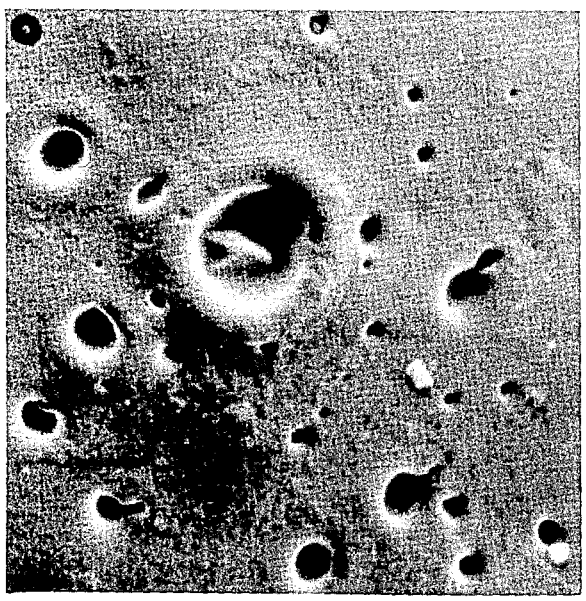
FIG. 3 is an enlargement of a portion of one of the beads of FIG. 1 and shows the presence of the varcuoles normally filled with solution B. Of course, most of the vacuoles shown on the photographs have broken due to the pressure developed in the inside thereof when subjected to the vacuum of the electron-microscope.

The beads were subjected to calibrate with a wire mesh for selecting the beads in the range of 100$\mu$ diameter. Then, the selected beads were uniformly deposited as a continuous monolayer (each bead substantially touching its neighbors) on an auto-adhesive plastic strip (type EGAFIX made by R. BURKHART, Lucerne, Switzerland) so as to obtain a strip in accordance with the invention.

The strips obtained as described were dipped for one second into solutions of glucose of various concentrations (shown below) and the color was allowed to develop for one minute after which a color reading was made. The color was due to the oxidation of o-tolidine by the peroxidase catalyzed action of the $H_2O_2$ liberated by the glucose-oxidase catalyzed oxidation of glucose, thus producing a blue indicator dye. The results are shown below:

| Glucose solutions (concentration g/l) | Colors of the strips |
|---|---|
| 1 | very light blue |
| 2,5 | light blue |
| 5 | medium blue |
| 10 | deep blue |

It is important to note that for reproducible results, the color readings must be taken at given intervals after dipping the strips because at the time of reading the reaction is not yet terminated and some of the glucose is not consumed yet be.

The above described strips were very stable when stored under normal dry conditions. The membranous wall of the vacuoles being semi-permeable, the enzymes were efficiently trapped therein because of their molecular weight which was too high for the enzymes to filter out through said semipermeable membrane.

EXAMPLE 2

Beads were prepared as described in Example 1 but omiting the o-tolidine in the polymer solution. This indicator was added afterwards to the dried beads by impregnating the beads with a solution of o-tolidine in toluene and subsequent drying. Then, test strips were prepared with the beads as described in Example 1 and behaved identically under field uses.

EXAMPLE 3

The procedure of Example 1 was repeated but with the following variation: solution A of the polymer was made from 4 g cellulose triacetate, 0.5 g of "Tween 20", 1 g of $TiO_2$ and 50 ml of $CH_2Cl_2$. The beads were prepared and used for making test strips exactly as in Example 1. When the strips were tested with glucose solutions they gave equally good results but with enhanced color contrast.

EXAMPLE 4

A first organic solution was prepared by mixing together: $CH_2Cl_2$ 25 ml; sodium-lauryl sulfate 0.5 g; cellulose triacetate 2 g; cumene hydroperoxide 0.5 g; 6-methoxyquinoline 0.16 g; ethylene glycol (stabilizer) 0.5 g.

This solution was emulsified in 400 ml of 0.1 M acetate buffer (pH 5.8) containing 0.5 g of sodium-lauryl sulfate; then it was evaporated as described in Example 1 to give beads of a first type (C) which were filtered and dried.

A second type of beads (D) were prepared the same way but using as the organic solution the following mixture:

$CH_2Cl_2$ 25 ml; cellulose triacetate 1 g; sodium-lauryl sulfate 0.5 g; o-tolidine 0.25 g. The disperion aqueous phaase was the same as above.

Thereafter strips were prepared as described in Example 1 using a 1/1 by weight mixture of beads C and D. The test strips thus prepared were tested to determine traces of blood in aqueous solutions. The test mechanism is the same as that discussed in connection with U.S. Pat. No. 3,092,463 and is based on the ability of some components of blood (hemoglobin constituents) to catalyze the transfer of oxygen from the peroxide to the o-tolidine with consecutive formation of the blue dye. The following results were obtained:

| Hemoglobin conc. (mg/l) | Color of the strip (After one min) |
|---|---|
| 0.923 | light blue |
| 6.16 | blue |

The above Examples shall not be considered as limiting as many other strip types can be prepared for measuring other biologically produced substances such as galactose, cholesterol, ketone compounds and bilirubine. Further, the strips can be applied to many other domains where the rapid checking of water solution is important, e.g. chemical synthesis, plating, surface finishing, etc.

Also strips can easily be made with one kind of bead system on one side and another kind on the other side for measuring selectively two different components in a solution.

One factor is very important and should always be carefully considered in manufacturing beads suitable for the present invention when the beads contain a water solution of a water soluble component. In order to be within rapid reach of the solution to be analyzed, the vacuoles containing the water solution must be rather near the surface of the beads but, of course, not too much otherwise the vacuoles will not resist accidental bursting. In other words, the wall separating the vacuoles from the outside will have to be strong enough to conform with the mechanical strength specifications required for the present beads but thin enough to allow the diffusion of the substances to be analyzed within a reasonable time. Now, such wall thickness can actually be controlled by properly adjusting the osmotic factors of (a) the solution to be incorporated in the beads and (b) the water phase serving as a final dispersion phase in the manufacture of the beads. Such osmotic factors will be kept within acceptable limits when the ratio of the molar concentration of the ingredients of the first water phase to that of the ingredients of the second water-phase is from about 1/5:5/1.

Beyond the lower limit, the entrapping yield may be low and the vacuoles may be distributed too far from the periphery of the beads which may result in having the color reaction to develop too slowly to be practical. On the otherhand when the upper limit of this range is exceeded, there is a risk that the external wall of the vacuoles becomes too thin (the external water will tend to penetrate into the beads to dilute the trapped solution) and the vacuoles might partially break during preparation or under storage with consequent loss of part of the encapsulated products.

EXAMPLE 5

An organic solution (O) of cellulose triacetate was prepared by dissolving under agitation 2 g of the granulated polymer in 25 ml of $CH_2Cl_2$ containing 0.1 g of "Tween 20" and 0.25 g of o-tolidine. Then a first water phase W1 was prepared by measuring and mixing successively 3.5 ml of glucose oxidase solution (1000 International Units/ml), 60 mg of peroxidase, 133.8 mg of trisodium citrate and 51.4 mg of citric acid, the two latter ingredient being first mixed together in the dry state before dissolving. Then the first water phase W1 was emulsified in the organic solution at room temperature and high speed until a regular emulsion W1/O is obtained (drops of the waterphase about 1–5 μm dispersed in the organic solution). During this operation, cooling may be necessary in order to avoid heating and possible denaturation of the enzymes.

In the meantime, the three following second waterphase solutions (W2a, W2b and W2c) were prepared by dissolving the following ingredients in 350 ml of distilled $H_2O$.

| Ingredients | W2a | W2b | W2c |
|---|---|---|---|
| Trisodium citrate | 6.69 g | 13.38 g (0.13M) | 26.76 g |
| Citric acid | 2.8 g | 5.4 g (0.07M) | 10.8 g |
| $(NH_4)_2SO_4$ | 2.31 g | 4.62 g (0.13M) | 9.24 g |
| Sodium lauryl-sulfate | 202 mg | 202 mg | 202 mg |
| Water to make | 350 ml | 350 ml | 350 ml |

Then the emulsion W1/O was dispersed in W2b by adding W1/O slowly and with rapid stirring into W2b.

After the addition was complete, stirring was continued and the temperature was gradually raised to 40° C. while a stream of nitrogen was swept over the surface of the agitated dispersion until the methylene chloride was removed by evaporation. The resulting suspension of polymer beads was filtered and dried and the filtered water phase was analyzed for residual untrapped enzyme (glucose oxidase) by usual means. It was found that only 3% of the originally used glucose oxidase was not trapped within the beads which called for high trapping efficiency.

The above dispersion step was repeated with new lots of W1/O emulsion using the above water phases W2a and W2c. In such cases the encapsulation yields for the enzymes were 72% and 82% respectively. This indicates that the best results are obtained when the buffer concentrations in the first and the second water phase are about equivalent.

EXAMPLE 6

Preparation of a test-strip for ascertaining the presence of catalase in cows milk The presence of catalase in the milk of ruminant is a sign of disease and a simple method for detecting the enzyme helps in detecting such diseases at an early easily curable stage. The reactions involved in the present strip are the following splitting the milk lactose into galactose with galactosidase, oxidizing the galactose in the catalysis presence of galactose oxidase, thus producing hydrogen peroxide, decomposing the $H_2O_2$ into water and $O_2$ by the catalase possibly present and ascertaining the residual $H_2O_2$ present by its action on o-tolidine in the presence of peroxidase (same color reaction as in the previous Examples).

Four grams of cellulose triacetate and 0.02 g of o-tolidine were dissolved in 50 ml of $CH_2Cl_2$ with 0.4 g of "Tween 20". The solution was divided into two equal ml portions called E1 and E2.

Then a first water phase (F1) was prepared by dissolving 10 I.U. of catalase free β-galactosidase and 150 I.U. of catalase free β-galactose oxidase into 3.5 ml of 0.1 M phosphate buffer (pH 7.5) containing some magnesium chloride (0.003 M $MgCl_2$).

Another water phase (F2) was prepared identically with 100 I.U. of peroxidase in 3.5 ml of the same phosphate-$MgCl_2$ buffer. Then, F1 was emulsified with E1 under the same conditions described at Example 1 in the case of emulsifying B in A; and F2 was emulsified with E2 identically.

Afterwards, the compositions F1/E1 and F2/E2 were gently mixed together (to avoid the microdrops of E1 collapsing with that of E2) and the mixture was dispersed in a third water phase G which was made by dissolving the following ingredients:

Sodium lauryl sulfate 0.2 g; ammonium sulfate 4.6 g; 0.1 M phosphate buffer (pH 7.5) 350 ml. The obtained dispersion was subjected to evaporation under nitrogen as described in Example 4, after which beads of polymer were obtained (50–120μ) which contained tiny vacuoles (1–5μ) of two kinds. The first kind contained the first water phase F1 and the second kind contained the second water phase F2. The vacuoles of the two kinds were homogeneously and statistically distributed within the periphery of the beads.

Then the beads were calibrated and applied on the surface of an adhesive strip as in the previous Examples.

When the strips were used to test the milk of healthy or infected animals, the lactose dissolved in the milk was allowed to react with the enzymes of F1 whereupon $H_2O_2$ was liberated. Then the solution containing the catalase and the $H_2O_2$ migrated from the first type of vacuoles to the second type in which the $H_2O_2$, having not yet been destroyed by the catalase, oxidized the tolidine because of the presence of the catalase. The color development after one minute was therefore inversely proportional to the original concentration of the catalase in the infected milk. In the case of healthy cows, the color was very deep blue. In the case of cows with heavy mastitis, the strip kept colorless or very pale blue.

I claim:

1. A test strip for analyzing for a substance dissolved in an aqueous test solution which can be a biological fluid, said test strip comprising:

an inert nonabsorbent base strip forming a support; and a layer of solid spherical hydrophilic beads composed of a semipermeable polymer and coated onto and bonded to at least one surface of said support, said beads being in mutually contacting relationship in said layer to define pockets between mutually contacting beads and said support in which reproducible quantities of aqueous test solution can be retained, said beads being formed with microvacuoles containing at least one reagent located within the beads and retained therein such that said substance or a compound generated by said substance can penetrate into said beads to effect a color-change of said beads.

a plurality of reagents being provided in said beads at sites and under conditions such that the different reagents are held apart during storage and being allowed to react mutually only upon contact with said test solution.

2. The test strip defined in claim 1 wherein one of said reagents is water soluble and another of said reagents is water insoluble, the water insoluble reagent being present in dissolved form within the polymer, the water soluble reagent being received in vacuoles of the beads.

3. The test strip defined in claim 1 wherein said membrane has a thickness of substantially 0.1 to 1 micron.

4. The test strip defined in claim 1 wherein said support is opaque and light reflective.

5. The test strip defined in claim 1 wherein said beads are translucent.

6. The test strip defined in claim 1 wherein said beads contain titanium dioxide pigment.

7. The test strip defined in claim 1 wherein said layer comprises beads of two different types, the beads of one type differing from the beads of the other type by containing a different reagent in the microvacuoles thereof.

* * * * *